(12) United States Patent
Toth et al.

(10) Patent No.: US 7,907,757 B2
(45) Date of Patent: Mar. 15, 2011

(54) METHODS AND APPARATUS FOR NEW USEFUL METRICS

(75) Inventors: Thomas Louis Toth, Brookfield, WI (US); Bernice Eland Hoppel, Delafield, WI (US); Rendon Clive Nelson, Chapel Hill, NC (US); James George Colsher, Durham, NC (US); Timothy Garvey Turkington, Durham, NC (US); Lisa Mei-ling Ho, Durham, NC (US)

(73) Assignees: General Electric Company, Schenectady, NY (US); Duke University, Durham, NC (US)

( * ) Notice: Subject to any disclaimer, the term of this patent is extended or adjusted under 35 U.S.C. 154(b) by 1146 days.

(21) Appl. No.: 11/563,121

(22) Filed: Nov. 24, 2006

(65) Prior Publication Data

US 2008/0123920 A1    May 29, 2008

Related U.S. Application Data

(63) Continuation-in-part of application No. 11/485,136, filed on Jul. 12, 2006, now Pat. No. 7,822,253.

(51) Int. Cl.
*G06K 9/00* (2006.01)
*A61B 6/00* (2006.01)
*G01N 23/00* (2006.01)
*G21K 1/12* (2006.01)
*H05G 1/60* (2006.01)

(52) U.S. Cl. ............. 382/128; 382/131; 378/4; 378/21; 378/54

(58) Field of Classification Search .............. 382/128, 382/131; 378/4, 16, 20, 21, 53, 54, 156
See application file for complete search history.

(56) References Cited

U.S. PATENT DOCUMENTS

| | | | | |
|---|---|---|---|---|
| 6,990,171 B2 | 1/2006 | Toth et al. | | 378/16 |
| 7,068,750 B2 | 6/2006 | Toth et al. | | 378/16 |
| 7,068,751 B2 | 6/2006 | Toth et al. | | 378/20 |
| 7,558,364 B2 * | 7/2009 | Lin | | 378/16 |
| 2002/0065460 A1 * | 5/2002 | Murao | | 600/425 |
| 2004/0068181 A1 * | 4/2004 | Takeyama | | 600/425 |
| 2008/0013813 A1 * | 1/2008 | Joshi et al. | | 382/131 |

OTHER PUBLICATIONS

Huda et al., "Patient size and x-ray technique factors in head computed tomography examinations," Med. Phys. vol. 31, Issue 3, pp. 595-601, Mar. 2004.*
Author: Toth et al.; Title: The Influence of Bowtie Filter Selection, Patient Size and Patient Centering on CT Dose and Image Noise; Item: Medical Physics; vol. 33, No. 6; Program: SU-FF-I-42; Date: Jun. 2006; pp. 1 (p. 2006).
U.S. Appl. No. 11/485,136, filed Jul. 12, 2006, Joshi et al.
U.S. Appl. No. 11/287,029, filed Nov. 23, 2005, unknown.

* cited by examiner

*Primary Examiner* — John B Strege
(74) *Attorney, Agent, or Firm* — ZPS Group, SC

(57) ABSTRACT

A computer readable medium is embedded with a program configured to receive or generate a PAI, and/or use the PAI in a diagnostic application.

25 Claims, 6 Drawing Sheets sqrtPA ~ 302

$$sqrtPA = \sqrt{\sum P(i)}$$

sqrtIAA ~ 304

$image(x,y)$ $I(x, y) = (image(x, y)/1000 + 1) \times PixelArea$ $$sqrtIAA = \sqrt{\sum I(x, y)}$$

METHODS AND APPARATUS FOR NEW USEFUL METRICS

CROSS-REFERENCE TO RELATED APPLICATIONS

This application is a continuation-in-part (CIP) of patent application Ser. No. 11/485,136 filed Jul. 12, 2006 now U.S. Pat. No. 7,822,253 titled Methods and Apparatus for BMD Measuring, which is hereby incorporated in its entirety.

BACKGROUND OF THE INVENTION

This invention relates generally to imaging methods and apparatus, and more particularly, to methods and apparatus that provide non-scanner dependent patient specific data.

Patient characteristics such as, for example, but not limited to, weight, height, girth, diameter, body mass index, gender, age etc. can be used by physicians to attempt to determine the probability of a specific disease, to help establish the proper operating parameters for a medical procedure such as, for example not limited to, the obtaining of a diagnostic image and/or to help in the interpretation of diagnostic images or other diagnostic information or data. Such characterizations may be only loosely related or indirectly represent factors that are significant to the problem. For example, the patient's weight might be used to determine the tube current for a CT or x-ray procedure even though the patient's attenuation derived from a scout scan provides a more accurate deterministic function for the determination of the proper tube current (auto exposure control). Similarly, with PET/CT it is more important to note the density and size of the patient (rather than the weight) in determining the activity of the agents to be used and the imaging time. Knowledge of the regional density of the patient can provide valuable information to the physician.

It is contemplated that patient x-ray attenuation information can be employed as a patient factor that can be used to improve the outcome for a wide variety of medical diagnostic and treatment problems. Therefore described below are methods and apparatus that provide for scanner independent patient specific x-ray attenuation data. As used herein scanner independent means the same as non-scanner dependent.

BRIEF DESCRIPTION OF THE INVENTION

In one aspect, a computer readable medium is embedded with a program configured to receive or generate a Patent Attenuation Information (PAI), and/or use the PAI in a diagnostic application.

In another aspect, a method includes using a PAI as a metric other than to determine a bowtie filter.

In yet another aspect, a computer readable medium is embedded with a program configured to instruct a computer to perform a statistical correlation between at least one PAI and a disease probability.

In yet still another, a system includes an x-ray source, an x-ray detector positioned to receive x-rays emitted from the source, and a computer a computer coupled to the detector either directly, or indirectly over a network or otherwise. The computer is configured to receive or generate a PAI and use the PAI in an imaging application.

In still yet another aspect, a method includes obtaining a series of measurements taken over time of a density of an object, and statistically equalizing any change in density of the object.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray system, it is contemplated that the benefits of the invention accrue to all diagnostic imaging systems and modalities such as PET, MRI, SPECT, Ultrasound, fused systems such as a CT/PET system, and/or any modality yet to be developed in which patient attenuation is a factor. As used herein "patient attenuation" refers to any patient induced disturbance or loss of energy such as relaxation properties of hydrogen nuclei in MRI, positron emission distribution in PET, gamma ray emission in nuclear medicine, and deflection of acoustic energy in ultrasound etc.

Figure 1:
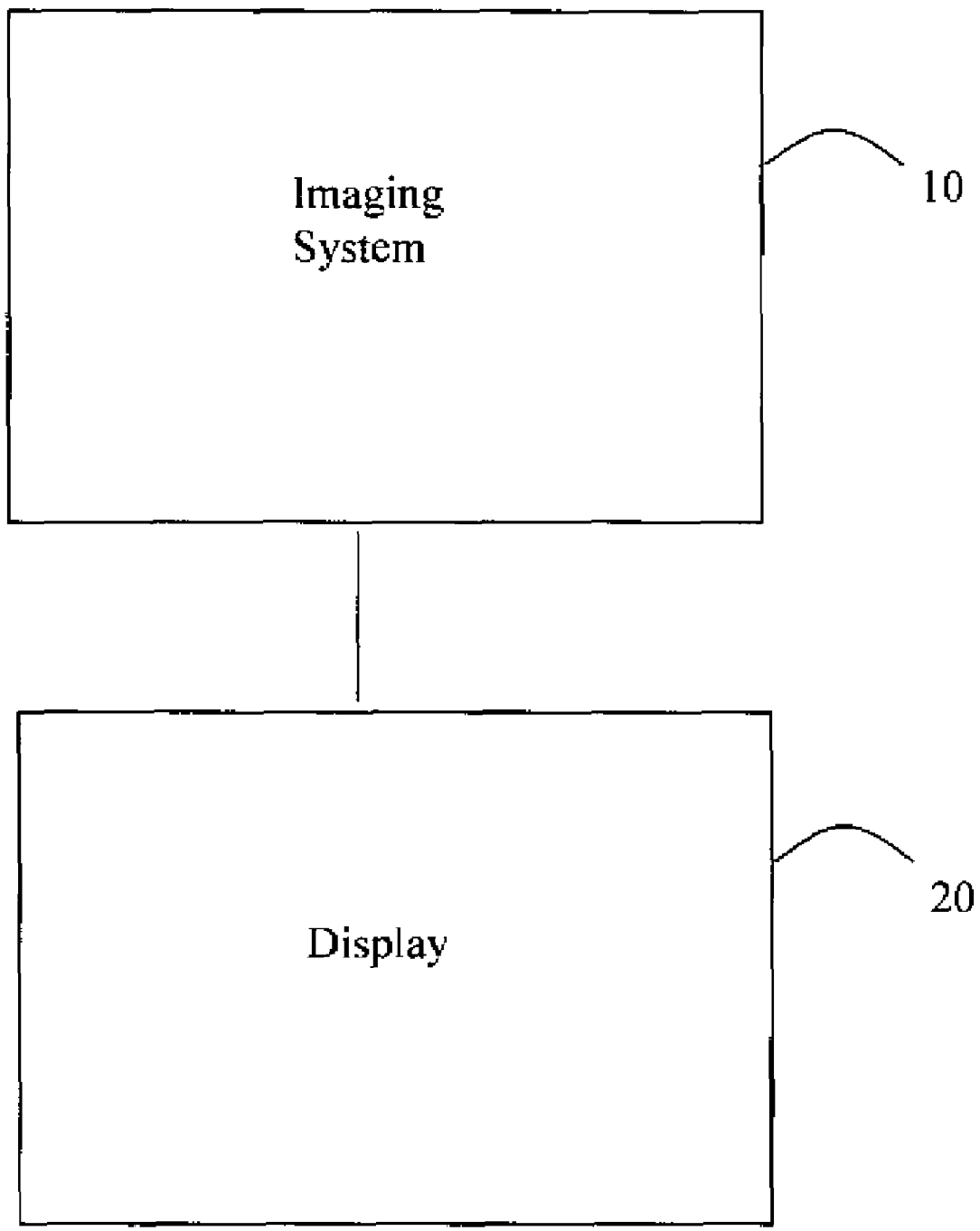
FIG. 1 illustrates an exemplary diagnostic imaging system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and the below described obtainment/attainment of a non-scanner dependent patient specific metric can be done in one modality (e.g., CT) and the processed data can be transferred to the other modality (e.g., PET). Display 20 can be separate from system 10 or integrated with system 10. System 10 includes an acquisition device such as an x-ray radiation detector, a Gamma Camera, an ultrasound probe and/or an MRI coil.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center as shown in FIG. 2.

Figure 2:
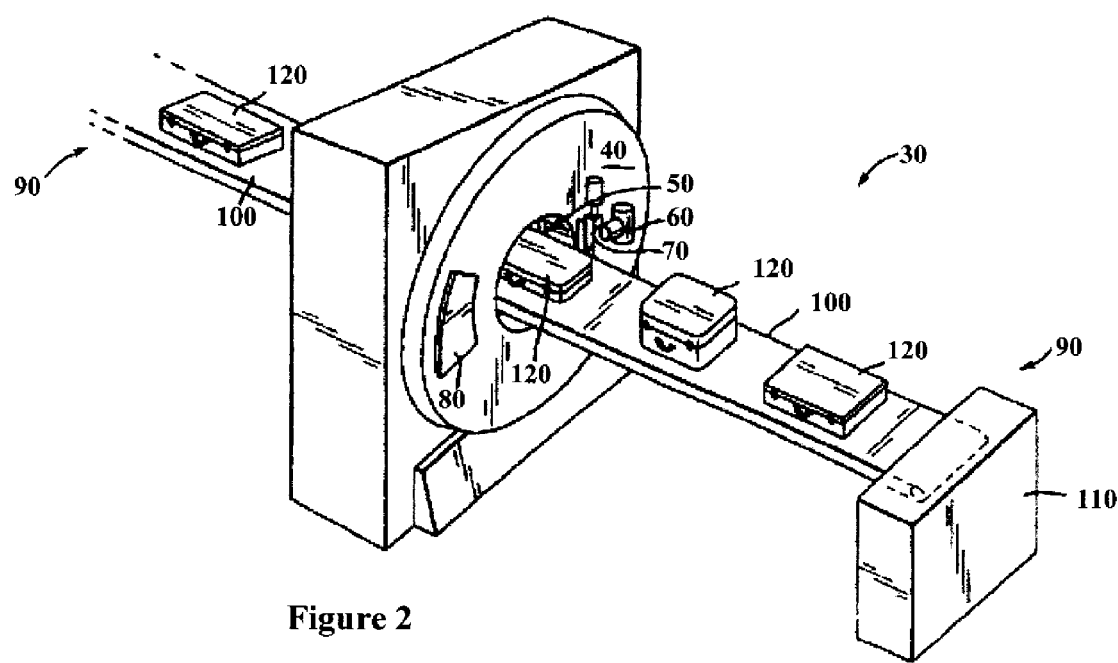
FIG. 2 illustrates a package/baggage inspection system.

Referring now to FIG. 2, a package/baggage inspection system 30 includes a rotatable gantry 40 having an opening 50 therein through which packages or pieces of baggage may pass. The rotatable gantry 50 houses a high frequency electromagnetic energy source 60 aligned with an attenuation filter 70 as well as a detector assembly 80. A conveyor system 90 is also provided and includes a conveyor belt 100 supported by structure 110 to automatically and continuously pass packages or baggage pieces 120 through opening 50 to be scanned. Objects 120 are fed through opening 50 by conveyor belt 100, imaging data is then acquired, and the conveyor belt 100 removes the packages 120 from opening 50 in a controlled and continuous manner. As a result, postal inspectors, baggage handlers, and other security personnel may non-invasively inspect the contents of packages 120 for explosives, knives, guns, contraband, and the like.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Figure 3:
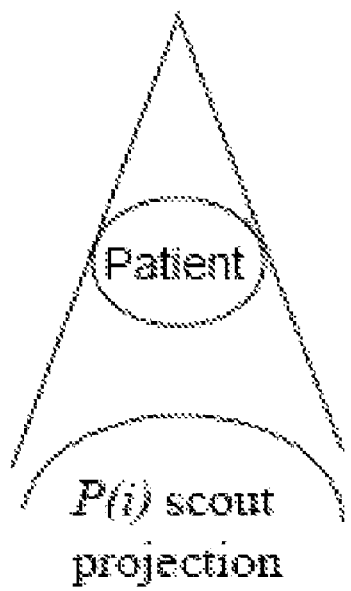
FIG. 3 illustrates the PAI in terms of the square root of the projection area from a scout image (sqrtPA) and the square root of the image attenuation area (sqrtIAA) from a CT image.
Figure 3:
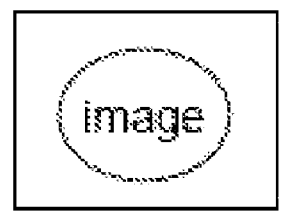

Patient attenuation information (PAI) can be derived from a scout scan, a digital x-ray image, and/or a CT image. FIG. 3 illustrates the PAI in terms of the square root of the projection area from a scout image (sqrtPA) 302 and the square root of the image attenuation area (sqrtIAA) 304 from a CT image. The sqrtIAA is a patient attenuation metric that is independent of scanner make and model and hence could become a standard metric. Note the relationship between (sqrtPA) and (sqrtIAA) where (sqrtIAA)≅s*sqrtPA where S is=1/sample density per cm.

The sqrtPA is scanner dependent but it can be translated to the sqrtIAA using a scale factor as shown in FIG. 3, and/or by using the scanner's sampling geometry. See FIG. 6 and note that the scale factor that relates PA to IAA is approximated as the mean isocenter sample spacing. One could be more precise in calculating IAA by summing a weighted set of projection values using the actual sample spacing for each value $(SI \times (\tan(\alpha_{n+0.5}) - \tan(\alpha_{n-0.5}))$ where: SI is the source to isocenter distance, n is the ray sample number relative to isocenter and a is the sample angle. And an off center patient simply changes the effective SI sample increment.

The sqrtPA is scanner dependent but it can be translated to the sqrtIAA using patient centering information to compute a more accurate translation. Methods to determine patient miscentering are in U.S. Pat. No. 7,068,750. Note that a PAI can be calculated from a conventional digital X-ray C-arm system in the same manner as a CT scout since they are virtually identical imaging representations although pixel sizes are typically much smaller. It should be noted that the herein described methods and apparatus are equally suited for micro CT or micro x-ray systems used for animal research and industrial applications as well.

Figure 4:
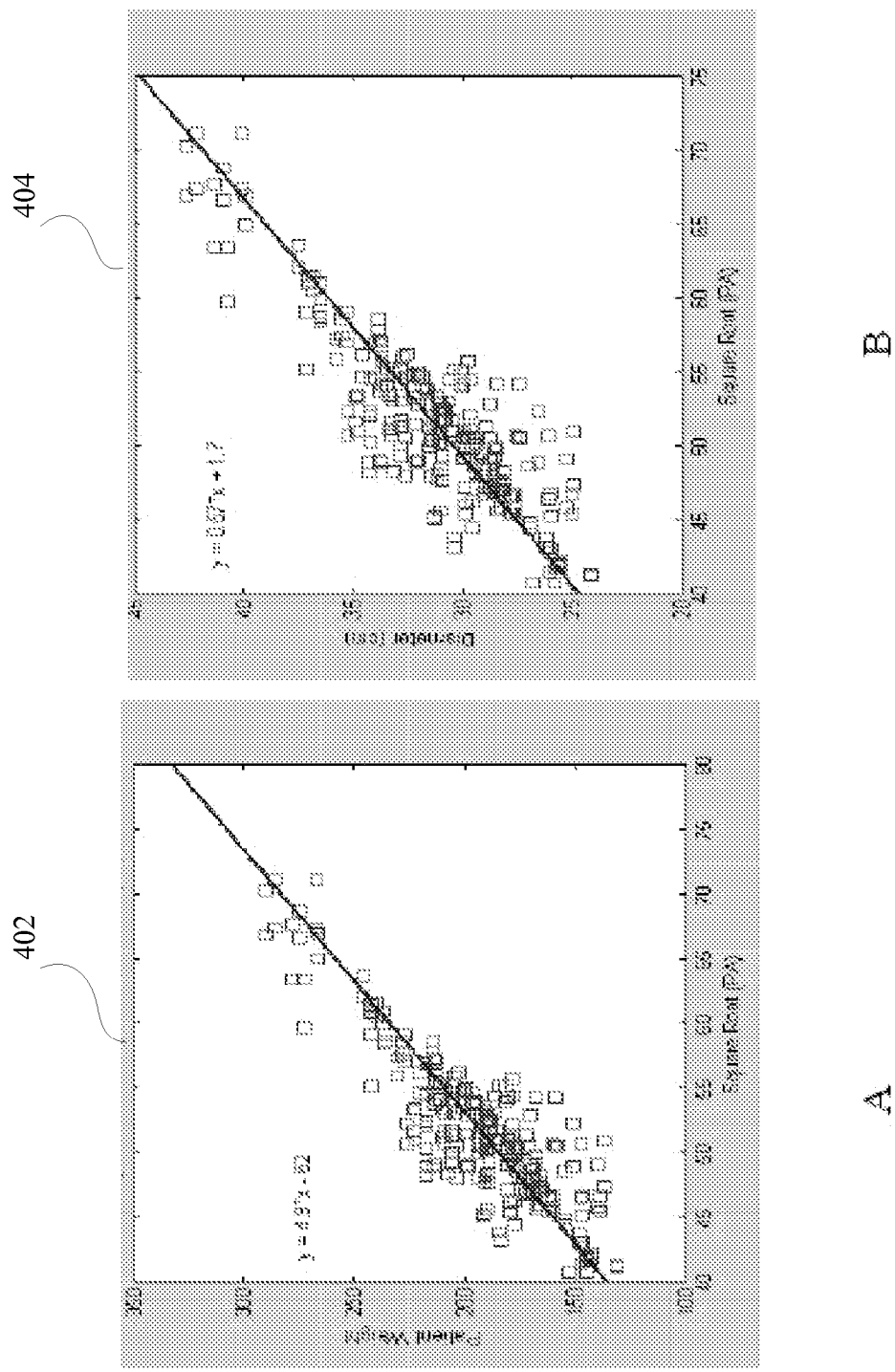
FIG. 4 illustrates that the square root (sqrtPA) may be employed to provide convenient values that correlate linearly with patient weight and diameter measurements.

FIG. 4 illustrates that the square root (sqrtPA) may be employed to provide convenient values that correlate linearly with patient weight 402 and diameter 404 measurements. Additionally, patient attenuation information can be determined as the mean for a specific region of the patient (abdomen, chest, pelvis, etc.) for better correlation with the desired medical problem to be solved. This can be done automatically using methods such as those described in co-pending patent application Ser. No. 11/287,029, filed Nov. 23, 2005. Some example medical applications for using a patient attenuation index (PAT) are described below. The patient attenuation information can be used as an index and therefore PAI refers to both patient attenuation index and patient attenuation information.

A normalizing function for diagnostic analysis is one example medical application. When analyzing diagnostic functional information including a plurality of abnormal values, the size of the patient is important in determining which values are truly abnormal. Not only does the circumference of the patient have clinical relevance but also the density of the region of interest (ROI) or the difference between having a large amount of bone and muscle compared to fat in the ROI. The PAI is a useful metric for normalizing functional data such as myocardial volume, ejection fraction, and wall thickness. For example, athletes with a great deal of muscular structure might have a slightly larger heart or ejection fraction, which is perfectly normal compared to a smaller female, which has a smaller heart to match her stature. Therefore, by accounting for the natural differences in PAI between a male athlete and a female, false positives and/or false negatives can be avoided. This same idea is useful in both CT imaging as well as SPECT and PET imaging. Muscular chest walls and bony structures (male athlete) would cause more absorption/scatter of positrons and photons than a less dense wall (female) would cause.

The determination of contrast load is another example medical application. The amount and rate of contrast media used for a patient scan is of high concern since iodinated contrast media is toxic. There is a trade off to minimize contrast to minimize allergic reaction risk, kidney risk, and cost of contrast used vs. using sufficient contrast to obtain an appropriate diagnostic quality scan. The PAI from a scout can be used to provide more accurate contrast load information.

The determination of isotope load is another example medical application. Similar to CT, in PET and SPECT imaging, it is desirable to get the optimal dose to the patient. Knowing the density of the individual can improve the quality of the images by allowing for a more accurate dose calculation as well as the optimization of the amount of time, which is spent in a single bed position. For example, the thoracic region, which is full of air will take less time to complete compared with a muscular abdominal region. Optimizing the table and the dose can decrease the amount of time the patient is required to stay on the bed as well as the best image quality for a given dose. Additionally, agents which are used in short-lived perfusion imaging such as Rb, O-15, N-13 can be optimized to have the optimal dose for the patient size and the arterial input function can be related to the density of the patient as well as their weight.

Computed Tomography Dose Indexing (CTDI) is a standard dose measurement methodology required to be utilized by all computed tomography manufactures. One methodology utilizes phantoms for reporting typical head and body dosages. Other standard dose measurements include the "weighted" CTDI (CTDIW or CTDIw), the "volume" CTDI (CTDIVOL or CTDIvol), the "multiple scan average dose" (MSAD), and the "dose-length product" (DLP). Newer regulations require the CTDIvol to be displayed to the operator after selecting the scan but before executing the scan. Some methodologies for determining the CTDIvol commonly utilize assumptions regarding patient size to provide such estimated CTDIvols prior to imaging. CTDI100 refers to the dosimetric quantity in computed tomography (CT) can be assessed using a pencil ionization chamber with an active length of 100 mm. CTDIw refers to the weighted average CTDI in a scan plane. In one embodiment, an application uses the PAI to adjust a representation of x-ray dose in accordance with patient size. The representation of x-ray dose may be one or more of CTDIvol, CTDIw, and CTDI100.

The modulation of x-ray beam, energy and/or amplitude is another example application. This metric is also valuable in determining the optimal energy and current of the x-ray beam depending on where it is in the body. The upper chest and shoulders are more dense and will need more energy and current to produce the same image quality compared with that of the middle and lower thoracic region which is comprised of mostly air. Modulation of the beam is a common occurrence with ECG signals and shape of the patient. The attenuation measure would make this modulation much more accurate since patients can have very large regions in the lower abdomen but have very little attenuation in that region and therefore need only minimal current. As used herein the term "electric based parameter" means any scanning parameter or an image parameter that is either user controlled or computer controlled including parameters, such as, for example, but not limited to, a scan time, a tube current, a helical pitch, kVp, and/or a Hounsfield unit scale adjustment.

The adjustment of scan times is another example medical application. This metric is also valuable in determining the scan times in PET and SPECT. Times can be adjusted for each patient and can also be adjusted between bed positions to account for differing attenuations between patients and between cross sections of the same patient.

Another example medical application is a HU scale adjustment based on PAI. CT values are represented by the Hounsfield scale, but they are not absolute numbers since they vary as a function of tissue material composition (especially for high atomic number elements such as calcium and iodinated contrast) and with effective energy of the system and overall attenuation of the patient. In spite of this, clinicians have used HU values to make clinical decisions regarding a diagnosis. The PAI can be used to as a normalizing factor to help reduce the variability of CT values to these confounding factors and thereby provide increased diagnostic confidence in quantitative CT (QCT) diagnostic applications. An example of this is given in co-pending patent application Ser. No. 11/485,136 filed Jul. 12, 2006 titled Methods and Apparatus for BMD Measuring.

Another example medical application is in performing calibration corrections. CT, SPECT, and PET can all benefit from the use of a metric that will allow for a more accurate calibration of scatter and absorption compared with using a standard phantom. The density of the patient can create various artifacts with the images that can be corrected for. Calibrations are completed before the images are reconstructed and therefore the density of the patient would be available to improve the overall appearance of the images.

Figure 5:
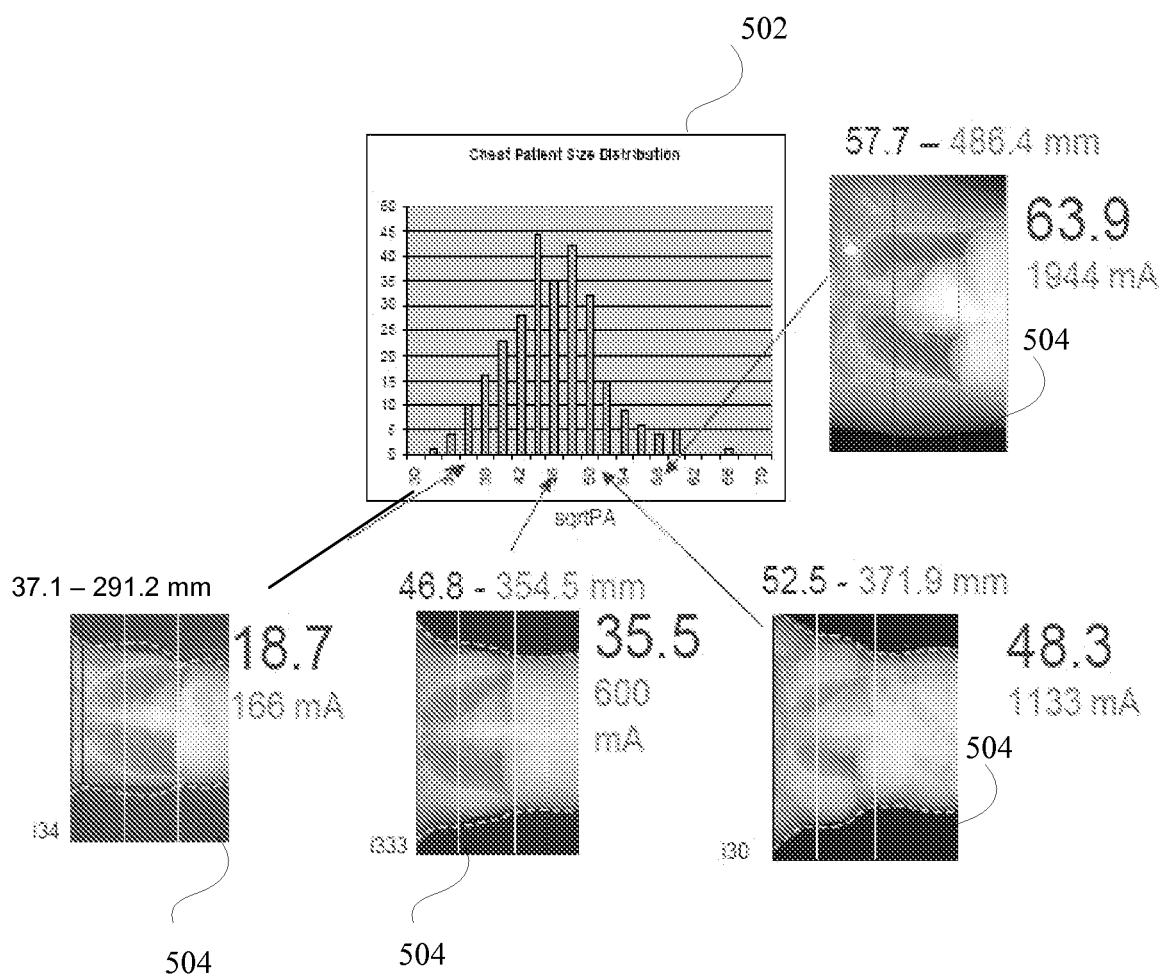
FIG. 5 illustrates that a patient's PAI value relative to the population distribution can be used to correlate it with disease probability.
Figure 6:
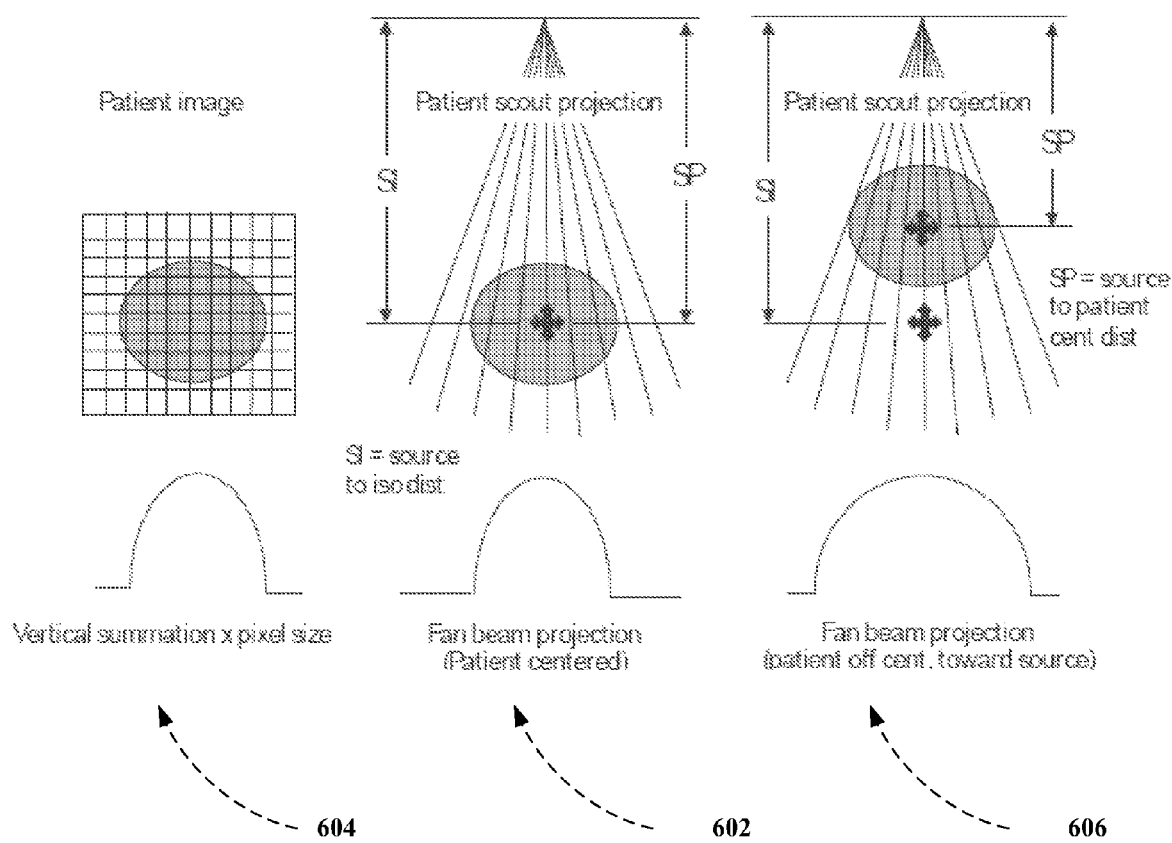
FIG. 6 illustrates how one may use a scanner's sampling geometry to calculate a PAI.

Another example medical application is statistical correlations. Patient characteristics can be predictors of disease probability. For example, obesity correlates with increased heart disease, diabetes, etc. A patient's PAI value relative to the population distribution (FIGS. 4 and 5) can be used to correlate with disease probability. One could develop application specific attenuation metrics such as an approximate ratio of lung volume to PAI (see patient scout images in FIG. 5). FIG. 5 illustrates a chest patient size distribution 502 and images 504. FIG. 6 illustrates how one may use a scanner's sampling geometry to calculate a PAI. A fan beam projection (patient centered) is illustrated at 602, a vertical summation at 604, and a fan beam projection (patient off centered) at 606. Where for 604, IAA=projection summation*sample spacing (pixel size), for 602 PA=projection summation, and for 606 PA=Sample spacing decreases (Projection summation*SP/SI). Note that for a typical cardiac scan the scan parameters are 120 kv, 600 mA, 0.35 seconds, and 0.625 mm. Referring back to FIG. 5, for each imager the size (sqrtPA) is provided first, then the lateral diameter in mm, the noise at 600 mA, and then the required mA for a 35.5 noise index is given. For example, referring to the lower left image, the size is 37.1, the lateral diameter is 291.2 mm, the noise is 18.7, and the mA is 166.

Technical effects include that the herein described methods and apparatus use the PAI in a medical application to improve image quality in reconstructed images. Another technical effect is the ability to increase diagnoses accuracy using the PAIs. Both improving image quality and increasing diagnosis accuracy are typical medical applications as is dose reduction to the patient. Therefore, as used herein the term "medical application" is meant to mean any application in a medical setting other than for the determination of a bowtie filter. Additionally, image quality improvement is likely desirable in a non-medical setting such as is illustrated in FIG. 2. Therefore, as used herein the term "imaging application" means all medical applications as set forth above and all non-medical applications as well. Additionally, because there are not patients in a non-medical setting, PAI also means object attenuation information (OAI), where the object takes the place of the patient in PAI. Lastly, an index will be obtained with a plurality of PAIs so that the new metric may be used to learn new correlations, and as used herein that index of patient attenuation (i.e., a Patient Attenuation Index (PAI)) is also referred to herein as PAI. In other words, PAI refers to both a single patient's attenuation (for example when used regarding a bolus's amount, agent used, and/or timing) and to a collection of many patients' attenuations (for example when doing statistical correlations). Another technical effect is the ability to obtain a series of measurements taken over time of a density of an object and to statistically equalize any change in density of the object. This statistical equalization could be applied not only to medical imaging but also to plastics, glass, and metals.

As used herein the term "Diagnostic application" refers to any computer application or software for the diagnosis of a problem within a system with a dependent factor being the density of the system, i.e., a medical diagnosis for kidney disease, which may be dependent on the obesity of the patient. As used herein, diagnostic includes all prognostic applications as well.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A CT system comprising:
   a rotatable gantry having an opening to receive a patient to be scanned;
   a high frequency electromagnetic energy projection source configured to project a high frequency electromagnetic energy beam toward the patient;
   a detector assembly configured to detect high frequency electromagnetic energy passing through the patient; and
   a computer programmed to:
      receive imaging data from the detector assembly, the imaging data comprising at least one of a scout scan projection area (PA) and an image attenuation area (IAA);
      determine a patient attenuation information (PAI) value based on the imaging data, the PAI value being a square root of one of the PA (sqrtPA) and the IAA (sqrtIAA);
      determine a density of at least one region-of-interest in the patient based on the PAI value
      analyze and store the density for use in a subsequent diagnostic application.

2. The CT system of claim 1 wherein the computer is further programmed to calculate the IAA according to:

$$IAA = s \times PA$$

where s=1/sample density per cm.

3. The CT system of claim 1 wherein the computer is further programmed to calculate the IAA according to:

$$IAA = SI \times (\tan(\alpha_{n+0.5}) - \tan(\alpha_{n-0.5}))$$

where SI is a source to isocenter distance, n is a ray sample number relative to isocenter, and $\alpha$ is a sample angle.

4. The CT system of claim 1 wherein the computer is further programmed to calculate the IAA according to:

$$IAA = I(x,y) = (image(x,y)/1000+1) \times pixel\ area.$$

5. The CT system of claim 1 wherein the computer is further programmed to analyze the density of the at least one region-of-interest to determine at least one of an appropriate x-ray beam energy and current and a scan time for the patient.

6. The CT system of claim 1 wherein the computer is further programmed to analyze the density of the at least one region-of-interest to calibrate the CT system to account for scatter and absorption of the high frequency electromagnetic energy beam as determined by the density of the at least one region-of-interest.

7. The CT system of claim 1 wherein the computer is further programmed to analyze the density of the at least one region-of-interest to determine at least one of an amount, timing, and flow rate of an x-ray contrast enhancement bolus to provide to the patient and an amount of radioactive isotope to provide to the patient.

8. The CT system of claim 1 wherein the computer is further programmed to:
   analyze the PAI value;
   compare the PAI value to a plurality of reference PAI values; and
   predict a probability of disease for the patient based on the comparison of the PAI value and the plurality of reference PAI values.

9. The CT system of claim 1 wherein the computer is further programmed to analyze the PAI value to normalize or statistically equalize a plurality of Hounsfield units in a CT image.

10. A method for determining a patient attenuation information (PAI) value from a CT scan, the method comprising:
    performing a CT scan on a subject by way of a CT imaging device so as to acquire imaging data on the subject;
    receiving the imaging data at a computer linked to the CT imaging device, the imaging data comprising at least one of a scout scan projection area (PA) and an image attenuation area (IAA);
    calculating, on the computer, the square root of the at least one of the PA and the IAA to determine a patient attenuation information (PAI) value;
    determining, on the computer, a density of at least one region-of-interest in the subject based on the PAI value; and
    storing the density of the at least one region-of-interest in the computer for use in a subsequent diagnostic application.

11. The method of claim 10 wherein, when the square root of the PA is calculated to determine the PAI, the method further comprises converting the square root of the PA into the square root of the IAA.

12. The method of claim 11 wherein the square root of the PA is converted based on one of a scale factor, a scanner sampling geometry, and patient centering information.

13. The method of claim 10 wherein the PAI correlates linearly with patient weight and diameter measurements.

14. A non-transitory computer readable storage medium having a computer program stored thereon and representing a set of instructions that when executed by a computer causes the computer to:
    receive imaging data on a subject from an imaging device, the imaging data comprising at least one of a scout scan projection area (PA) and an image attenuation area (IAA);
    calculate the square root of the at least one of the PA and the IAA to determine a patient attenuation information (PAI) value;
    determine a density of at least one region-of-interest in the subject based on the PAI value; and
    store the density of the at least one region-of-interest for use in a subsequent diagnostic application.

15. The computer readable storage medium of claim 14 wherein the set of instructions further causes the computer to calculate the IAA according to:

$$IAA = s \times PA$$

where s=1/sample density per cm.

16. The computer readable storage medium of claim 14 wherein the set of instructions further causes the computer to calculate the IAA according to:

$$IAA = SI \times (\tan(\alpha_{n+0.5}) - \tan(\alpha_{n-0.5}))$$

where SI is a source to isocenter distance, n is a ray sample number relative to isocenter, and α is a sample angle.

17. The computer readable storage medium of claim 14 wherein the set of instructions further causes the computer to calculate the IAA according to:

$$IAA = I(x,y) = (\text{image}(x,y)/1000 + 1) \times \text{pixel area}.$$

18. The computer readable storage medium of claim 14 wherein the set of instructions further causes the computer to set at least one scan parameter for a subsequent scan to be performed on the subject based on the density of the at least one region-of-interest.

19. A CT system comprising:
a rotatable gantry having an opening to receive a patient to be scanned;
a high frequency electromagnetic energy projection source configured to project a high frequency electromagnetic energy beam toward the patient;
a detector assembly configured to detect high frequency electromagnetic energy passing through the patient; and
a computer programmed to:
receive imaging data from the detector assembly, the imaging data comprising at least one of a scout scan projection area (PA) and an image attenuation area (IAA);
determine a patient attenuation information (PAI) value based on the imaging data, the PAI value being a square root of one of the PA (sqrtPA) and the IAA (sqrtIAA); and
analyze and store the PAI value for use in a subsequent diagnostic application;
wherein the computer is further programmed to calculate the IAA according to:

$$IAA = s \times PA$$

where s=1/sample density per cm.

20. A CT system comprising:
a rotatable gantry having an opening to receive a patient to be scanned;
a high frequency electromagnetic energy projection source configured to project a high frequency electromagnetic energy beam toward the patient;
a detector assembly configured to detect high frequency electromagnetic energy passing through the patient; and
a computer programmed to:
receive imaging data from the detector assembly, the imaging data comprising at least one of a scout scan projection area (PA) and an image attenuation area (IAA);
determine a patient attenuation information (PAI) value based on the imaging data, the PAI value being a square root of one of the PA (sqrtPA) and the IAA (sqrtIAA); and
analyze and store the PAI value for use in a subsequent diagnostic application;
wherein the computer is further programmed to calculate the IAA according to:

$$IAA = SI \times (\tan(\alpha_{n+0.5}) - \tan(\alpha_{n-0.5}))$$

where SI is a source to isocenter distance, n is a ray sample number relative to isocenter, and α is a sample angle.

21. A CT system comprising:
a rotatable gantry having an opening to receive a patient to be scanned;
a high frequency electromagnetic energy projection source configured to project a high frequency electromagnetic energy beam toward the patient;
a detector assembly configured to detect high frequency electromagnetic energy passing through the patient; and
a computer programmed to:
receive imaging data from the detector assembly, the imaging data comprising at least one of a scout scan projection area (PA) and an image attenuation area (IAA);
determine a patient attenuation information (PAI) value based on the imaging data, the PAI value being a square root of one of the PA (sqrtPA) and the IAA (sqrtIAA); and
analyze and store the PAI value for use in a subsequent diagnostic application;
wherein the computer is further programmed to calculate the IAA according to:

$$IAA = I(x,y) = (\text{image}(x,y)/1000 + 1) \times \text{pixel area}.$$

22. A CT system comprising:
a rotatable gantry having an opening to receive a patient to be scanned;
a high frequency electromagnetic energy projection source configured to project a high frequency electromagnetic energy beam toward the patient;
a detector assembly configured to detect high frequency electromagnetic energy passing through the patient; and
a computer programmed to:
receive imaging data from the detector assembly, the imaging data comprising at least one of a scout scan projection area (PA) and an image attenuation area (IAA);
determine a patient attenuation information (PAI) value based on the imaging data, the PAI value being a square root of one of the PA (sqrtPA) and the IAA (sqrtIAA);
analyze the PAI value;
compare the PAI value to a plurality of reference PAI values; and
predict a probability of disease for the patient based on the comparison of the PAI value and the plurality of reference PAI values.

23. A CT system comprising:
a rotatable gantry having an opening to receive a patient to be scanned;
a high frequency electromagnetic energy projection source configured to project a high frequency electromagnetic energy beam toward the patient;
a detector assembly configured to detect high frequency electromagnetic energy passing through the patient; and
a computer programmed to:
receive imaging data from the detector assembly, the imaging data comprising at least one of a scout scan projection area (PA) and an image attenuation area (IAA);
determine a patient attenuation information (PAI) value based on the imaging data, the PAI value being a square root of one of the PA (sqrtPA) and the IAA (sqrtIAA); and
analyze the PAI value to normalize or statistically equalize a plurality of Hounsfield units in a CT image.

24. A method for determining a patient attenuation information (PAI) value from a CT scan, the method comprising:
performing a CT scan on a subject by way of a CT imaging device so as to acquire imaging data on the subject;
receiving the imaging data at a computer linked to the CT imaging device, the imaging data comprising a scout scan projection area (PA);

calculating, on the computer, the square root of the PA to determine a patient attenuation information (PAI) value;
converting, on the computer, the square root of the PA into the square root of the IAA; and
storing the PAI value on the computer for use in a subsequent diagnostic application.

25. A method for determining a patient attenuation information (PAI) value from a CT scan, the method comprising:
performing a CT scan on a subject by way of a CT imaging device so as to acquire imaging data on the subject;
receiving the imaging data at a computer linked to the CT imaging device, the imaging data comprising at least one of a scout scan projection area (PA) and an image attenuation area (IAA);
calculating, on the computer, the square root of the at least one of the PA and the IAA to determine a patient attenuation information (PAI) value; and
storing the PAI value on the computer for use in a subsequent diagnostic application;
wherein the PAI value correlates linearly with patient weight and diameter measurements.

* * * * *